United States Patent
Meutermans et al.

(10) Patent No.: US 7,700,577 B2
(45) Date of Patent: Apr. 20, 2010

(54) CARBOHYDRATE BASED ANTI-BACTERIALS

(75) Inventors: Wim Meutermans, Toowong (AU); Giang Le Thanh, Mt Gravatt (AU); Giovani Abbenante, Sampsonvale (AU); Gerald Tometzki, Manly West (AU); George Adamson, Yately (GB); Bernd Becker, New Farm (AU); Matthias Grathwohl, Constance (DE); Premraj Rajaratnam, Eight Miles Palins (AU)

(73) Assignee: Alchemia Limited, Eight Miles Plains, Queensland (AU)

( * ) Notice: Subject to any disclaimer, the term of this patent is extended or adjusted under 35 U.S.C. 154(b) by 1015 days.

(21) Appl. No.: 10/531,303

(22) PCT Filed: Oct. 16, 2003

(86) PCT No.: PCT/AU03/01377
§ 371 (c)(1),
(2), (4) Date: Nov. 21, 2005

(87) PCT Pub. No.: WO2004/035062
PCT Pub. Date: Apr. 29, 2004

(65) Prior Publication Data
US 2006/0142217 A1 Jun. 29, 2006

(30) Foreign Application Priority Data
Oct. 17, 2002 (AU) ............... 2002952121

(51) Int. Cl.
A61K 31/715 (2006.01)
C07H 1/00 (2006.01)
A01N 25/34 (2006.01)
(52) U.S. Cl. .................. 514/53; 536/1.11; 424/404
(58) Field of Classification Search ............. 514/53; 536/1.11; 424/404
See application file for complete search history.

(56) References Cited

U.S. PATENT DOCUMENTS

| 5,414,073 A | * | 5/1995 | Okuyama et al. ......... 536/18.5 |
| 2006/0121530 A1 | | 6/2006 | Meutermans et al. |

FOREIGN PATENT DOCUMENTS

| WO | WO 97/34623 | 9/1997 |
| WO | WO 98/30570 | 7/1998 |
| WO | WO 98/38197 | 9/1998 |
| WO | 98/53813 | 12/1998 |
| WO | 99/26956 | 6/1999 |
| WO | 00/64915 | 11/2000 |
| WO | WO 01/51499 | 7/2001 |
| WO | WO 02/32963 | 4/2002 |

OTHER PUBLICATIONS

Merck Manual Home Edition, subject "Antibiotics". Retrieved on [Oct. 14, 2008]. Retrieved online from [http://www.merck.com/mmhe/print/sec17/ch192/ch192a.html].*
Oki, T., Tenmyo, O., Hirano, M., Tomatsu, K., Kamei, H. (1990) Pradimicins A, B and C: New Antifungal Antibiotics II. In Vitro and In Vivo biological Activities. The Journal of Antibiotics, vol. XLIII, No. 7, p. 763-770.*
Sawada, Y., Tsuno, T., Ueki, T., Yamamoto, H., Fukagawa, Y., Oki, T. (1993) Pradimicin Q, A New Pradimicin Aglycone, with alpha-Glucosidase Inhibitory Activity. The Journal of Antibiotics, vol. 46, No. 3, p. 507-510.*
Nishio, M., Ohkuma, H., Kakushima, M., Ohta, S.-I, Iimura, S., Hirano, M. Konishi, M., Oki, T. (1993) Synthesis and Antifungal Activities of Pradimicin A Derivatives Modification of the Alanine Moiety. The Journal of Antibiotics, vol. 46, No. 3, p. 494-499.*
International Search Report of PCT/AU03/01377 mailed Dec. 16, 2003.
Gruner et al, "Carbohydrate-Based Mimetics in Drug Design: Sugar Amino Acids and Carbohydrate Scaffolds", Chem. Rev. 102:491-514 (2002).
Chemical Abstracts Database, CAS Registry No. 135877-15-5, entered on Aug. 30, 1991.
Maeda et al, "Synthetic Studies on Sialoglycoconjugates 71: Synthesis of Sulfo- and Sialyl-Lewis X Epitope Analogs Containing the 1-Deoxy-N-Acetylglucosamine in Place of N-Acetylglucosamine Residue", Journal of Carbohydrate Chemistry 14(3):369-385 (1995).
Flitsch, "Glycosylation with a Twist", Nature 437:201-202 (2005).
Seeberger and Haase, "Solid-Phase Oligosaccharide Synthesis and Combinatorial Carbohydrate Libraries", Chemical Reviews 100(12):4349-4394 (2000).

* cited by examiner

*Primary Examiner*—Shaojia Anna Jiang
*Assistant Examiner*—Scarlett Goon
(74) *Attorney, Agent, or Firm*—Nixon & Vanderhye P.C.

(57) ABSTRACT

A method of inhibiting bacterial growth by contacting a bacteria with at least one disaccharide compound of General Formula I,

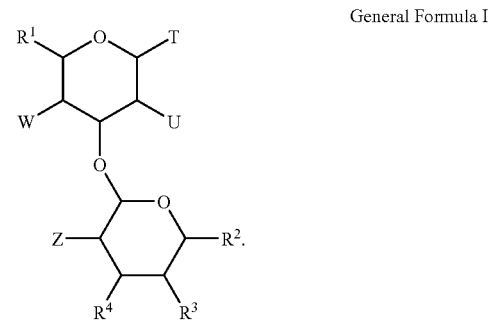

General Formula I 22 Claims, No Drawings

CARBOHYDRATE BASED ANTI-BACTERIALS

FIELD OF THE INVENTION

This application is the US national phase of international application PCT/AU2003/001377 filed 16 Oct. 2003, which designated the U.S. and claims benefit of AU 2002952121, dated 17 Oct. 2002, the entire contents of each of which are hereby incorporated by reference.

The invention relates to disaccharide compositions that have antibacterial properties.

BACKGROUND OF THE INVENTION

Bacteria have a great ability to generate resistance to drugs through lateral gene transfer, mutation of enzymes, or by expressing enzymes which actively pump out the drug or break it down. Over the past 10 years resistance to existing drugs has become a significant problem in many countries. No new antibacterial drugs have been developed over the past 15 years. Vancomycin is currently the drug of last resort to combat the multidrug resistant Gram-positive bacteria In many places vancomycin-resistant *Staphylococcus aureus* and Enterococci (VRE) have been discovered. There is thus a desperate need for a new antibacterial drug to replace the drug of last resort.

There are a host of cytoplasmic targets for the development of new antibacterials, such as gyrase inhibitors, protein synthesis inhibitors, muramyl cascade inhibitors and many more. The major hurdle in designing such drugs is that in addition to enzyme based activity these drugs need to cross the bacterial cell wall to exert their antibacterial effect. On the other hand, enzymes involved in the stage III synthesis of the bacterial cell wall exist on the cell wall exterior, and therefore drugs inhibiting these enzymes can exert their bactericidal or bacteriostatic effect without having to cross the cell wall. Penicillin, cephalosporin and vancomycin are drugs that act on the transpeptidase enzymes which control the final steps in the peptidoglycan biosynthesis. Moenomycin is known to act on the transglycosylase enzymes, which are similarly involved in the polymerization of disaccharide precursors. Moenomycin displays very high potency at MIC level, and is used in animal feed as a growth promoter.

Moenomycin is a lipid-linked pentasaccharide. Through extensive SAR experiments it was realised that smaller fragments of moenomycin were capable of exerting antibacterial activity. Trisaccharide fragments of moenomycin still display antibacterial activity, but are not sufficiently stable to be useful drugs. On the basis of this, Sofia and coworkers discovered a new series of disaccharides, carrying aromatic substituents in well defined positions around the disaccharide, which displayed significant MIC activity [WO0064915 and WO9926596].

A further class of disaccharide molecules, based on a substructure of vancomycin was shown to have antibacterial activity against vancomycin resistant bacteria. This class of molecules was subsequently demonstrated to contain transglycosylase inhibitors, and were not transpeptidase inhibitors as is vancomycin itself [WO9853813].

SUMMARY OF THE INVENTION

The present invention is directed to antibacterial compositions and is especially directed to a method of reducing bacterial growth by contacting bacteria with particular disaccharide like moieties.

The present invention may also be directed to an antibacterial pharmaceutical composition comprising a pharmaceutically acceptable carrier and a therapeutically effective amount of at least one particular disaccharide like moiety.

The present invention may also be directed to a method of screening such compounds for anti-bacterial activity by contacting the compounds with a Gram-positive or Gram-negative bacteria and monitoring the growth or growth inhibition of the bacteria.

In a first aspect, the invention provides a method of inhibiting bacterial growth by contacting a bacteria with at least one disaccharide compound of General Formula I,

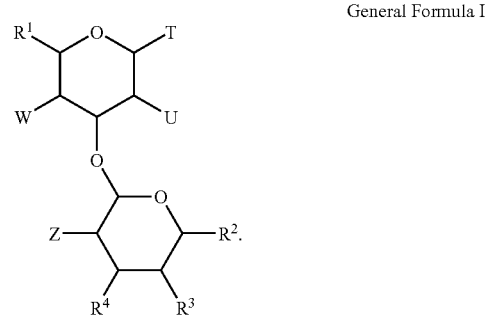

General Formula I

Wherein the pyranose rings may be of any configuration,

T is either R or —XR, where X is defined as oxygen, sulphur, NHC(O)—, and wherein R is selected from the non-limiting set comprised of H, or an alkyl, alkenyl, alkynyl, heteroalkyl aryl, heteroaryl, arylalkyl or heteroarylalkyl of 1 to 20 atoms which is optionally substituted, and can be branched or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl cycloalkyl, heteroalkyl, heteroaryl, aminoalkyl aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl aminoaryl aminoheteroaryl, thioalkyl thioaryl or thioheteroaryl, which may optionally be further substituted, U and Z independently selected from OR, NHR, NR(R) (where R may be the same or different), or the following non-limiting set,

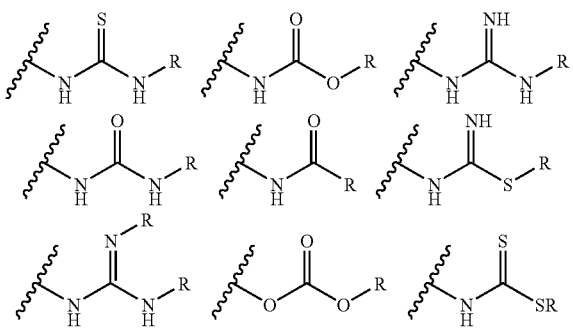

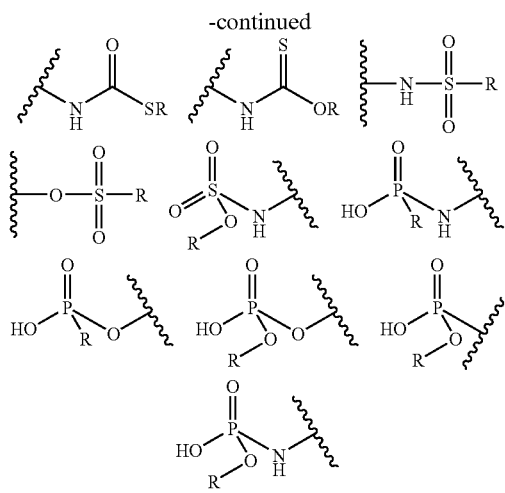

R[1] and R[2] are independently selected from H, CH$_3$, CH$_2$X, and C(O)NH,

R[3] and R[4] are independently selected from H, OH, OR, NHCOR, and

W is independently selected from OR$^L$, NHR$^L$, NR$^L$R, or the following the following non-limiting set,

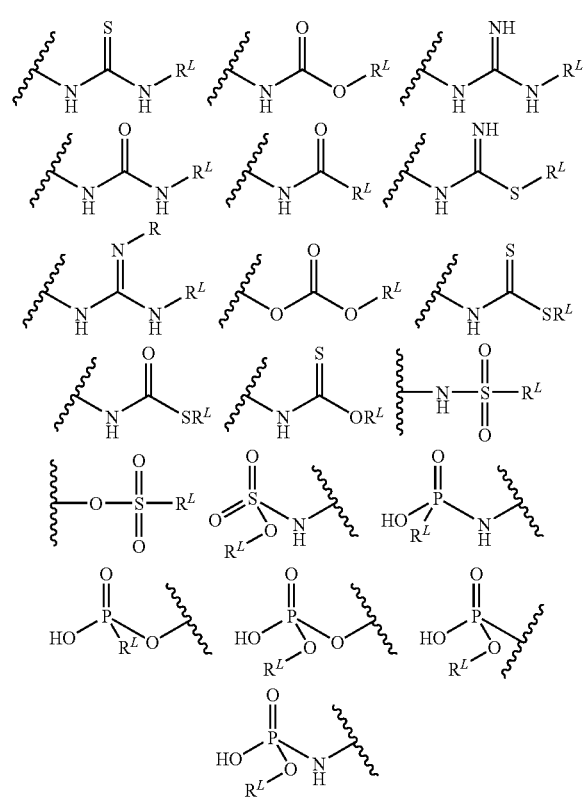

Wherein R$^L$ is a substituted or unsubstituted, linear or branched, saturated or unsaturated C3 to C55 alkyl, heteroalkyl, arylalkyl, alkylaryl chain. Substituents may include but are not limited to acidic groups such as carboxylic acids, sulfonic acids, phosphoric acids, tetrazoles, or other carboxylic acid mimetics or basic groups such as amines, guanidines, amidines, imidazoles or other amine mimetics.

In a further aspect, the invention provides a method of inhibiting bacterial growth by contacting a bacteria with at least one disaccharide compound of General Formula II, General Formula II

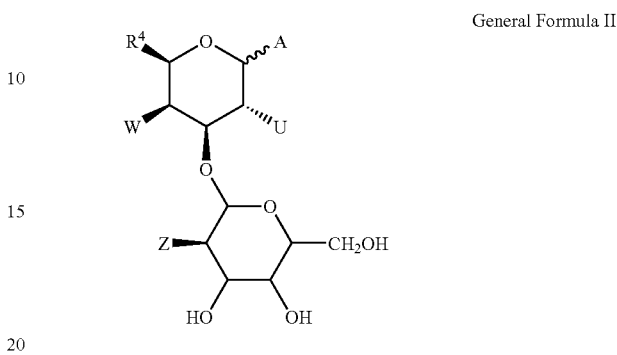

Wherein the disaccharide linkage is alpha or beta,
A is defined as hydrogen, OR or SR, and
R, U, W, Z and R[4] are defined as in General Formula I.

In a more preferred aspect, the invention provides a method of inhibiting bacterial growth by contacting a bacteria with at least one disaccharide compound of General Formula III, General Formula III

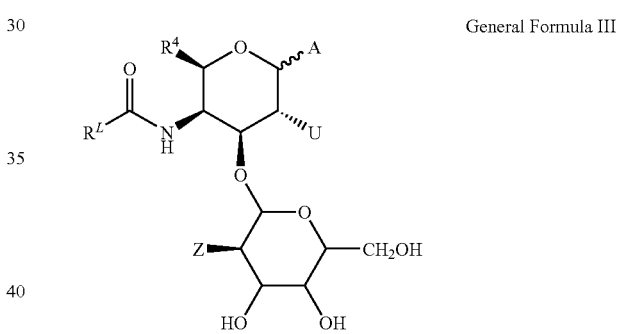

Wherein A is defined as in General Formula I, and
U, Z, R$^L$ and R[4] are defined as in General Formula I.

The bacterial may be Gram-positive or Gram-negative bacteria. The bacteria may comprise an *E-coli* bacteria, a Staphylococci Bacteria such as *Staphylococcus aureus*, or other bacteria such as *Micrococcus luteus* (ATCC272), *Staphylococcus aureus* (ATCC29213), *Staphylococcus aureus* (ATCC43300) MRSA, *Enterococcus faecalis* (ATCC29212), *Enterococcus faecalis* (ATCC51299) Vancomycin resistant and *Streptococcus pyogenes* (ATCC8668).

The method may comprise administering an effective amount of a compound of the first aspect, to a subject in need of such treatment. The subject may be a human, or may be a domestic, companion or zoo animal.

In another form, the invention may reside in an antibacterial composition comprising at least one compound as described above. The composition may comprise a pharmaceutical composition.

The compounds of the invention may be mixed with a pharmaceutical acceptable carrier, adjuvant, or vehicle which may comprise a-toxic carrier, adjuvant, or vehicle that may be administered to a patient, together with a compound of this invention, and which does not destroy the pharmacological activity thereof.

The pharmaceutical derivative may comprise a salt, ester, sit of an ester or other derivative of a compound of this invention which, upon administration to a recipient, is capable of providing, either directly or indirectly, a compound of this invention, although no limitation is meant thereby.

Compounds of the invention may be administered orally such as by means of a tabled, powder, liquid, emulsion, dispersion and the like; by inhalation; topically such as by means of a cream, ointment, salve etc; and as a suppository, although no limitation is meant thereby.

Methods and pharmaceutical carriers for preparation of pharmaceutical compositions are well known in the art, as set out in textbooks such as Remington's Pharmaceutical Sciences, 19th Edition, Mack Publishing Company, Easton, Pa., USA.

It will be clearly understood that, if a prior art publication is referred to herein, this reference does not constitute an admission that the publication forms part of the common general-knowledge in the art in Australia or in any other country.

Best Mode

MIC Testing:

The broth microdilution format of the National Committee for Clinical Laboratory Standards (NCCLS) approved standard for susceptibility tests as outlined in M7-A4 "methods for dillution Antimicrobial susceptibility tests for bacteria that grow aerobically; approved standard—fifth edition", January 2000 was utilized for minimum inhibitory concentration testing in Mueller-Hinton broth. The broth for *Streptococcus pyogenes* testing was supplemented with 2% laked horse blood. A positive result in initial testing was determined by complete inhibition of macroscopic bacterial growth at a concentration of 128 micrograms per mL after incubation for 16 to 24 hours at 37 degrees C. In the case of *Micrococcus luteus*, incubation was at 30 degrees C.

EXAMPLE 1

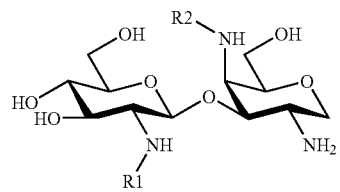

| Comp. No. | R1 | R2 | Mass | $R_f$ | SA24 | SA48 | EC24 |
|---|---|---|---|---|---|---|---|
| 1 | A5 | A9 | 679 | 4.62 | + | n.d. | − |

In all examples, + indicates an MIC value of less than 128 micrograms per mL, − indicates an MIC of greater then 128 micrograms per mL and n.d. indicates not determined.

Bacterial Types Are:
SA24 *S. aureus* after 24 hours exposure
SA48 *S. aureus* after 48 hours exposure
EC24 *E. coli* after 24 hours exposure

EXAMPLE 2

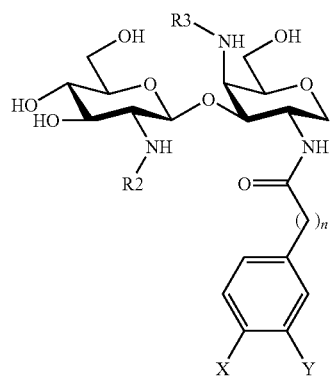

| Comp. No. | n | X | Y | R2 | R3 | MS | $R_f$ | SA24 | SA48 | EC24 |
|---|---|---|---|---|---|---|---|---|---|---|
| 2 | 1 | A1 | A10 | A11 | A7 | 875 | n.d | + | + | − |
| 3 | 1 | A1 | A10 | A4 | A9 | 831 | n.d | + | + | − |
| 4 | 0 | A1 | A10 | A12 | A9 | 800 | 5.1 | + | n.d | − |
| 5 | 0 | A1 | A10 | A5 | A7 | 862 | 4.92 | + | + | − |
| 6 | 0 | A1 | A10 | A5 | A9 | 851 | 5.36 | + | n.d | n.d. |
| 7 | 1 | A10 | A1 | A5 | A7 | 876 | 5.01 | + | + | − |

EXAMPLE 3

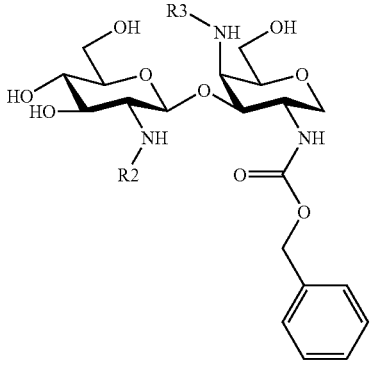

| Comp. No. | R2 | R3 | MW | $R_f$ | SA24 | SA48 | EC24 |
|---|---|---|---|---|---|---|---|
| 8 | A5 | A7 | 824 | 4.72 | + | + | − |
| 9 | A5 | A9 | 813 | 5.56 | + | n.d. | n.d. |

EXAMPLE 4

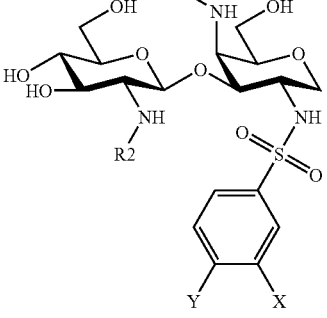

| Comp. No. | X | Y | R2 | R3 | MW | Rf | SA24 | SA48 | EC24 |
|---|---|---|---|---|---|---|---|---|---|
| 10 | A1 | A10 | A12 | A7 | 875 | n.d. | + | + | − |
| 11 | A1 | A10 | A4 | A9 | 831 | 5.18 | + | + | + |
| 12 | A1 | A10 | A4 | A7 | 843 | 4.65 | + | + | + |
| 13 | A1 | A10 | A4 | A1 | 663 | 3.2 | + | n.d. | n.d. |
| 14 | A1 | A10 | A5 | A9 | 864 | 5.27 | + | + | − |
| 15 | A1 | A10 | A19 | A9 | 863 | 4.85 | + | + | + |
| 16 | A1 | A10 | A19 | A7 | 875 | 4.23 | + | + | + |
| 19 | A1 | A10 | A19 | A25 | 849 | 4.8 | + | + | + |
| 20 | A1 | A10 | A19 | A22 | 861 | 3.49 | + | + | + |
| 21 | A1 | A10 | A19 | A16 | 889 | 3.57 | + | + | + |
| 22 | A1 | A10 | A19 | A23 | 930 | 5.1 | + | + | + |
| 23 | A1 | A10 | A19 | A26 | 831 | 3.56 | + | + | + |
| 24 | A1 | A10 | A19 | A27 | 899 | 4.22 | + | + | + |
| 25 | A1 | A10 | A19 | A28 | 904 | 3.3 | + | + | + |
| 26 | A1 | A10 | A19 | A29 | 918 | 3.5 | + | + | + |
| 27 | A14 | A1 | A2 | A9 | 800 | 5.01 | + | n.d. | + |
| 28 | A14 | A1 | A3 | A9 | 762 | 4.81 | + | n.d. | + |
| 29 | A14 | A1 | A12 | A9 | 764 | 4.92 | + | n.d. | + |
| 30 | A14 | A1 | A4 | A9 | 782 | 4.9 | + | n.d. | + |
| 31 | A14 | A1 | A15 | A9 | 765 | 5.4 | + | n.d. | + |

EXAMPLE 5

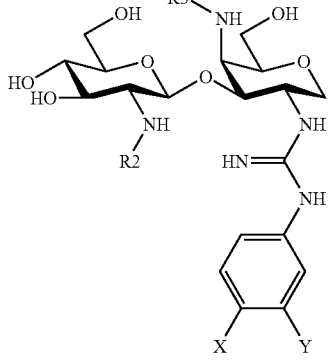

| Comp. No. | X | Y | R2 | R3 | MW | Rf | SA24 | SA48 | EC24 |
|---|---|---|---|---|---|---|---|---|---|
| 36 | A10 | A1 | A17 | A7 | 919 | n.d. | + | + | n.d. |
| 37 | A10 | A1 | A5 | A7 | 898 | 4.99 | + | + | − |
| 38 | A1 | A13 | A2 | A9 | 818 | 5.56 | + | n.d. | n.d. |
| 39 | A1 | A13 | A5 | A7 | 844 | 4.72 | + | + | − |
| 40 | A1 | A13 | A5 | A9 | 833 | 5.63 | + | n.d. | − |

EXAMPLE 6

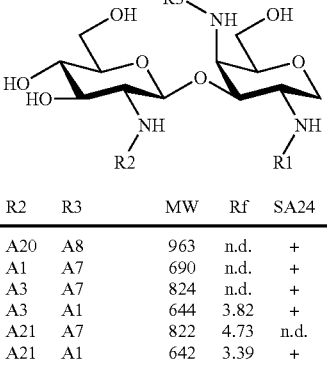

| Comp. No. | R1 | R2 | R3 | MW | Rf | SA24 | SA48 | EC24 |
|---|---|---|---|---|---|---|---|---|
| 42 | A20 | A20 | A8 | 963 | n.d. | + | n.d. | n.d. |
| 43 | A5 | A1 | A7 | 690 | n.d. | + | n.d. | n.d. |
| 44 | A5 | A3 | A7 | 824 | n.d. | + | + | n.d. |
| 45 | A5 | A3 | A1 | 644 | 3.82 | + | | n.d. |
| 46 | A5 | A21 | A7 | 822 | 4.73 | n.d. | + | − |
| 47 | A5 | A21 | A1 | 642 | 3.39 | + | n.d. | n.d. |
| 48 | A5 | A17 | A7 | 898 | n.d. | + | + | − |
| 49 | A5 | A4 | A7 | 844 | 4.9 | n.d. | + | − |
| 50 | A5 | A4 | A1 | 664 | 3.8 | + | n.d. | n.d. |
| 51 | A5 | A4 | A9 | | n.d. | n.d. | n.d. | n.d. |
| 52 | A5 | A44 | A7 | 823 | 3.98 | n.d. | + | − |
| 55 | A5 | A5 | A25 | 851 | 5.47 | + | + | n.d. |
| 56 | A5 | A5 | $C_{10}H_{21}$ | 837 | 5.38 | + | + | n.d. |
| 57 | A5 | A5 | A39 | 857 | 4.9 | + | + | n.d. |
| 58 | A5 | A5 | A40 | 861 | 5.01 | + | + | n.d. |
| 59 | A5 | A5 | A22 | | n.d. | + | + | − |
| 60 | A5 | A5 | bis-pentyl | 837 | 4.9 | + | + | n.d. |
| 61 | A5 | A5 | A32 | 851 | 5.56 | + | + | n.d. |
| 62 | A5 | A5 | A31 | 837 | 5.08 | + | + | n.d. |
| 63 | A5 | A5 | A30 | 823 | 5.1 | + | + | n.d. |
| 64 | A5 | A5 | A33 | 929 | 5.82 | + | + | n.d. |
| 65 | A5 | A5 | A34 | 942 | 5.17 | + | + | n.d. |
| 66 | A5 | A5 | A41 | 938 | 4.81 | − | n.d. | n.d. |
| 67 | A5 | A5 | A42 | 952 | 4.89 | − | n.d. | n.d. |
| 68 | A5 | A5 | A32 | 901 | 5.36 | − | n.d. | n.d. |
| 69 | A5 | A5 | A36 | 901 | 5.45 | + | n.d. | n.d. |
| 70 | A5 | A5 | A37 | 795 | 4.62 | − | n.d. | n.d. |
| 71 | A5 | A5 | A46 | 880 | 4.62 | − | n.d. | n.d. |
| 72 | A5 | A5 | A47 | 880 | 4.81 | − | n.d. | n.d. |
| 73 | A5 | A5 | A6 | 893 | 5.1 | + | n.d. | n.d. |
| 74 | A5 | A5 | A7 | 877 | 4.99 | + | n.d. | n.d. |

-continued

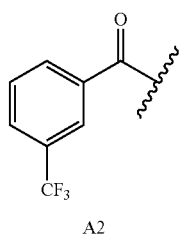

| Comp. | R1 | R2 | R3 | MW | Rf | SA24 | SA48 | EC24 |
|---|---|---|---|---|---|---|---|---|
| 75 | A5 | A5 | A23 | 932 | 5.63 | + | n.d. | n.d. |
| 76 | A5 | A5 | A8 | 893 | 6.09 | + | n.d. | n.d. |
| 77 | A5 | A5 | A9 | 865 | 5.63 | + | + | − |
| 78 | A5 | A3 | A9 | 813 | 5.45 | + | n.d. | n.d. |
| 79 | A5 | A4 | A9 | 833 | 5.73 | + | n.d. | n.d. |
| 80 | A18 | A4 | A9 | 744 | n.d. | + | n.d. | n.d. |

The following compounds were tested against additional organisims with the following results.
1. *Micrococcus luteus* (ATCC272)
2. *Staphylococcus aureus* (ATCC29213)
3. *Staphylococcus aureus* (ATCC43300) MRSA
4. *Enterococcus faecalis* (ATCC29212)
5. *Enterococcus faecalis* (ATCCS 1299) Vancomycin resistant
6. *Streptococcus pyogenes* (ATCC8668)

|  | Compound | | | | | |
|---|---|---|---|---|---|---|
|  | 1 | 2 | 3 | 4 | 5 | 6 |
| 76 | + | + | + | + | + | + |
| 42 | + | + | + | + | + | + |
| 75 | + | + | + | + | + | + |
| 68 | + | + | − | + | − | + |
| 65 | + | − | − | + | − | + |
| 69 | + | + | + | + | − | + |
| 70 | + | − | − | + | − | + |
| 73 | + | + | + | + | + | + |
| 74 | + | + | + | + | + | + |
| 66 | − | − | − | − | − | + |
| 67 | + | + | + | + | + | + |
| 77 | + | + | + | + | + | + |
| 51 | + | + | + | + | + | + |
| 56 | + | + | + | + | + | + |

TABLE 1

| Side Arms |
|---|
| 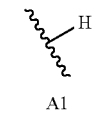<br>A1 |
| 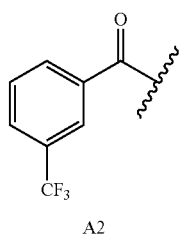 |

Note: continuing side arms

| Side Arms |
|---|
| 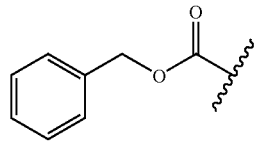<br>A3 |
| 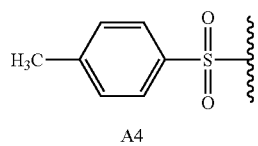<br>A4 |
| 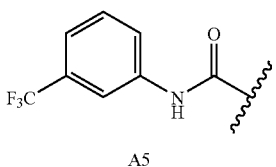<br>A5 |
| 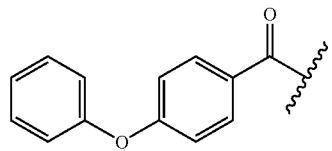<br>A6 |
| 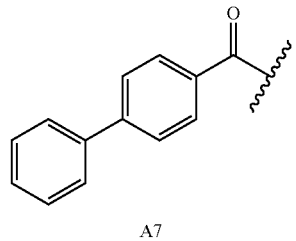<br>A7 |
| 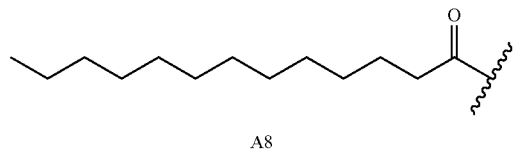<br>A8 |
| 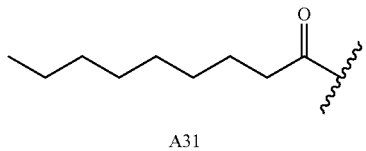<br>A31 |
| 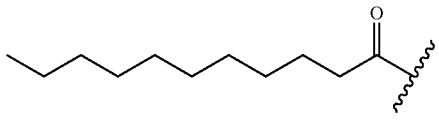<br>A9 |

A2

TABLE 1-continued
Side Arms
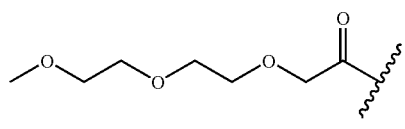
A38
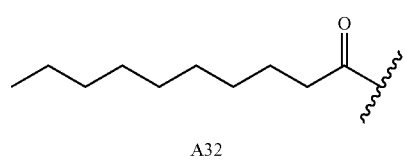
A32
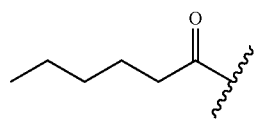
A37
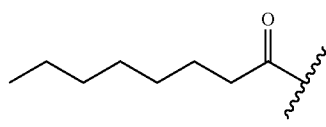
A30
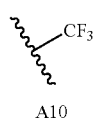
A10
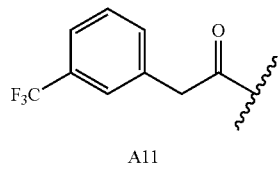
A11
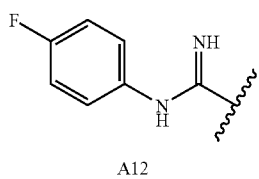
A12
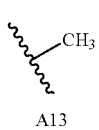
A13
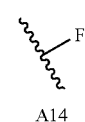
A14
TABLE 1-continued
Side Arms
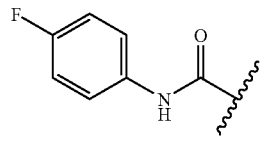
A15
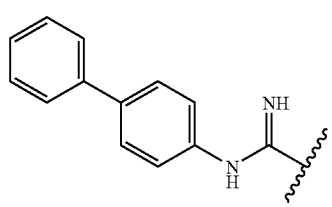
A16
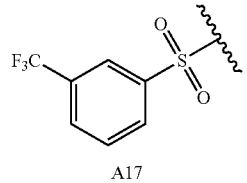
A17
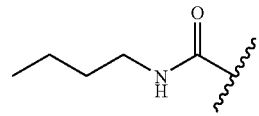
A18
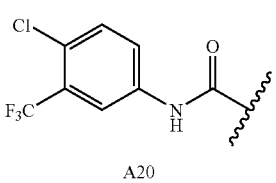
A20
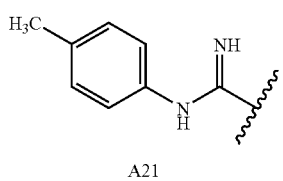
A21
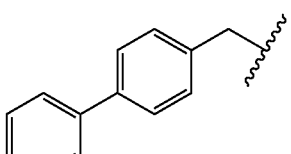
A22
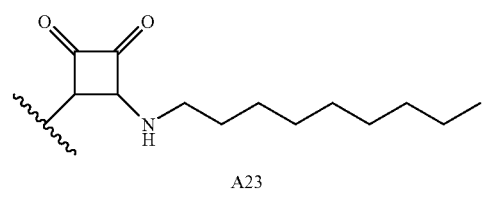
A23

TABLE 1-continued
Side Arms
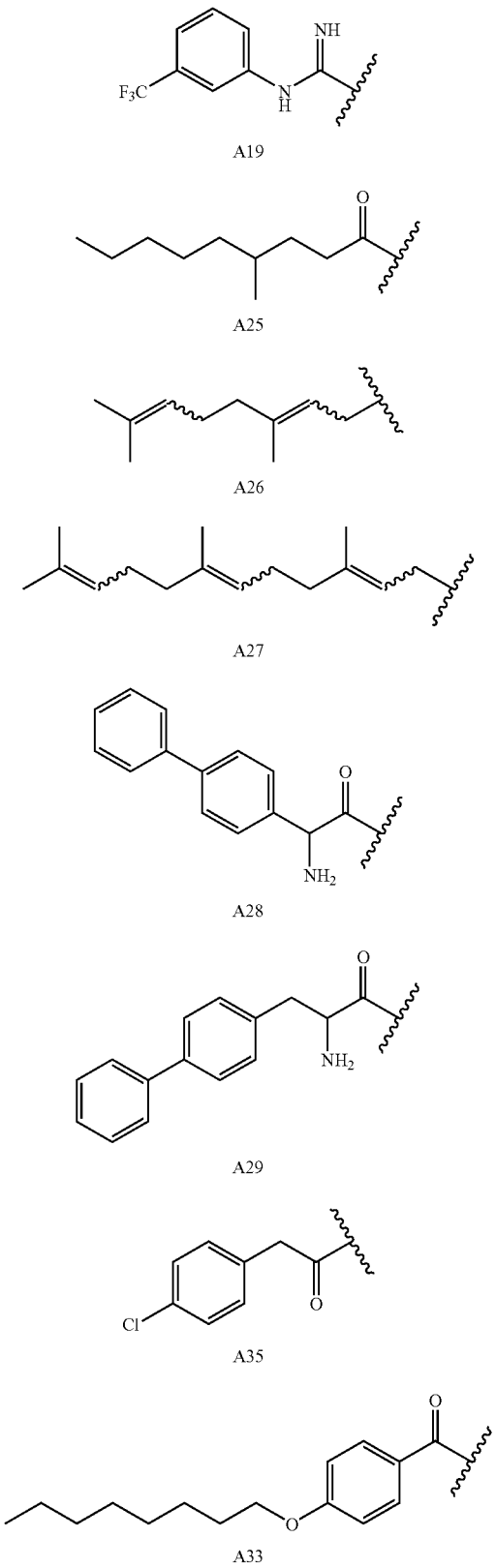
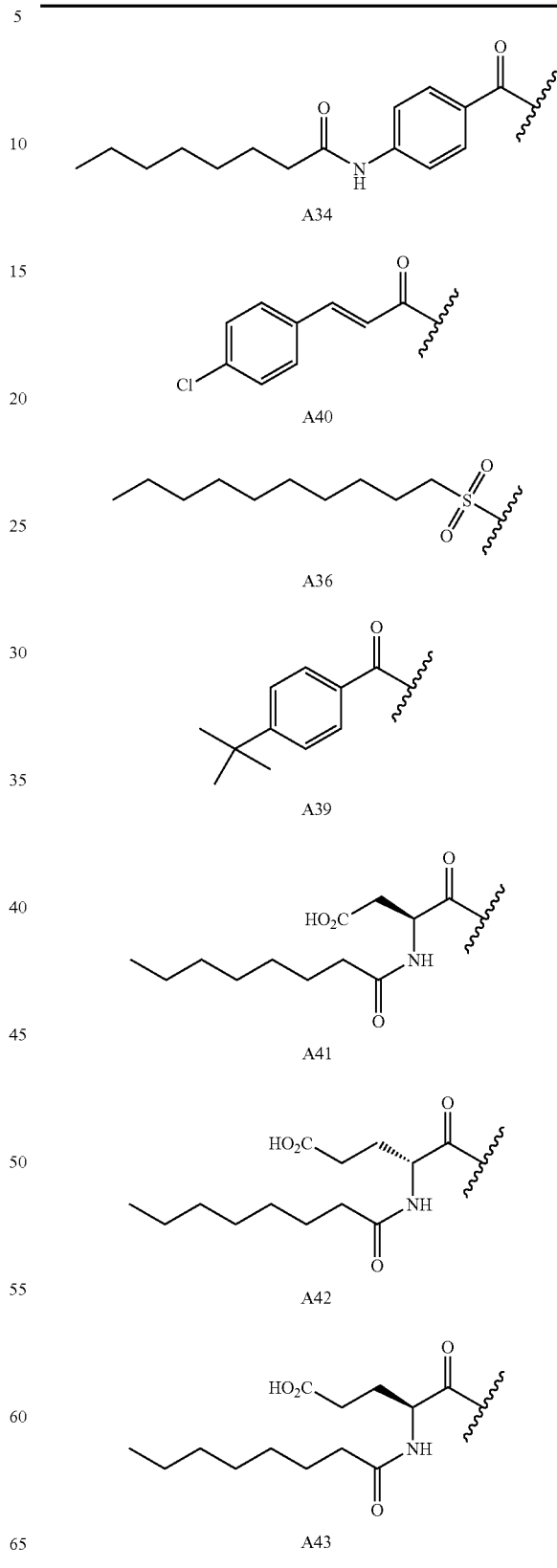

TABLE 1-continued

Side Arms

A44

A45

A46

A47

Throughout the specification and the claims unless the context requires otherwise, the term "comprise", or variations such as "comprises" or "comprising", will be understood to apply the inclusion of the stated integer or group of integers but not the exclusion of any other integer or group of integers.

It should be appreciated that various other changes and modifications can be made to any embodiment described without departing from the spirit and scope of the invention.

The invention claimed is:

1. A method of inhibiting bacterial growth comprising contacting a bacteria with at least one disaccharide compound of

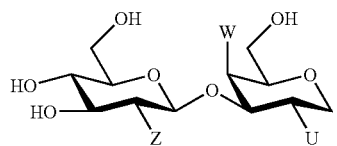

wherein

U and Z are independently selected from the group consisting of —OR, —NHR, —NR(R),

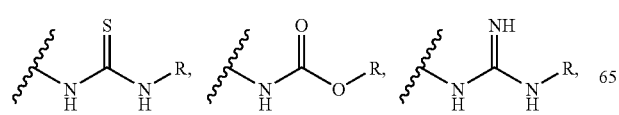

wherein R may be the same or different, R is a moiety of not more than 20 carbon atoms independently selected from the group consisting of: alkyl, alkenyl, alkynyl, heteroalkyl, aryl, heteroaryl, arylalkyl and heteroarylalkyl;

W is independently selected from the group consisting of —$OR^L$, —$NHR^L$, —$NR^LR$,

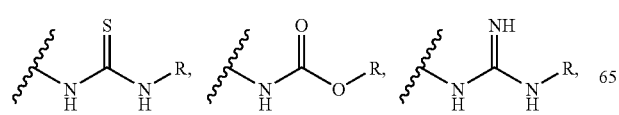

-continued

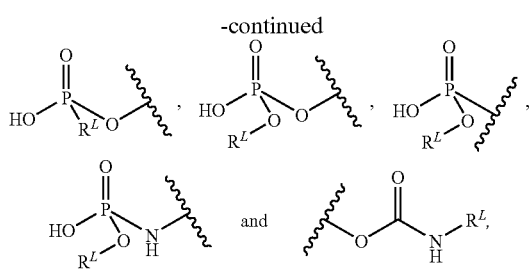

wherein $R^L$ is a substituted or unsubstituted, linear or branched moiety of between 3 and 55 carbon atoms selected from the group consisting of: alkyl, heteroalkyl, arylalkyl, and alkylaryl chain.

2. The method of claim 1, wherein $R^L$ is substituted by a moiety selected from the group consisting of: carboxylic acids, sulfonic acids, phosphoric acids, tetrazoles, amines, guanidiniums, amidines, imidazoles, and oxazoles.

3. The method of claim 1, wherein one or more R groups is substituted by a moiety selected from the group consisting of: —OH, —NO, —NO$_2$, —NH$_2$, —N$_3$, halogen, —CF$_3$, —CHF$_2$, —CH$_2$F, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, carbamoyl, aminoaryl, aminoheteroaryl, thioalkyl, thioaryl and thioheteroaryl.

4. The method of claim 1, wherein the compound is of

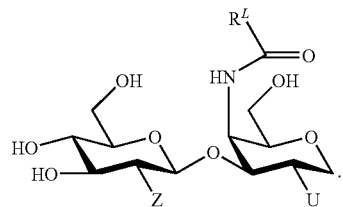

5. The method of claim 1, wherein the bacteria is a Gram+ bacteria.

6. The method of claim 1, wherein the bacteria is a Gram− bacteria.

7. The method of claim 1, wherein the bacteria is selected from the group consisting of an *Escherichia coli* (*E. coli*), *Micrococcus luteus*, *Staphylococcus aureus*, Methicillin-resistant *Staphylococcus aurcus* (MRSA), *Enterococcus faecalis*, *Enterococcus faecalis* Vancomycin resistant and *Streptococcus pyogenes*.

8. The method of claim 1, wherein the bacteria is *Staphylococcus aureus* and the compound is

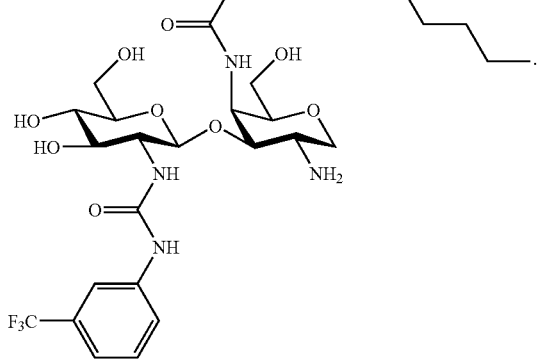

9. The method of claim 1, wherein the bacteria is *Staphylococcus aureus* and the compound is

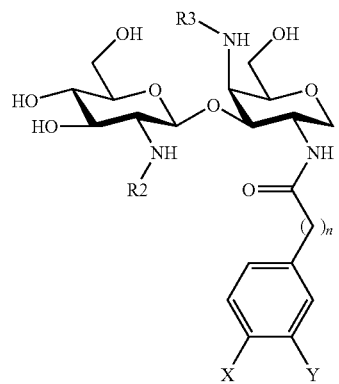

wherein:

| n | X | Y | R2 | R3 |
|---|---|---|----|----|
| 1 | H | CF$_3$ | ![F3C-phenyl-CH2-C(O)-] | ![-C(O)-biphenyl] |

| n | X | Y | R2 | R3 |
|---|---|---|---|---|
| 1 | H | CF₃ | 4-methylphenylsulfonyl | decanoyl |
| 0 | H | CF₃ | N-(4-fluorophenyl)amidino | decanoyl |
| 0 | H | CF₃ | 3-(trifluoromethyl)phenylaminocarbonyl | 4-biphenylcarbonyl |
| 0 | H | CF₃ | 3-(trifluoromethyl)phenylaminocarbonyl | decanoyl |
| 1 | CF₃ | H | 3-(trifluoromethyl)phenylaminocarbonyl | 4-biphenylcarbonyl |

10. The method of claim 1, wherein the bacteria is *Staphylococcus aureus* and the compound is

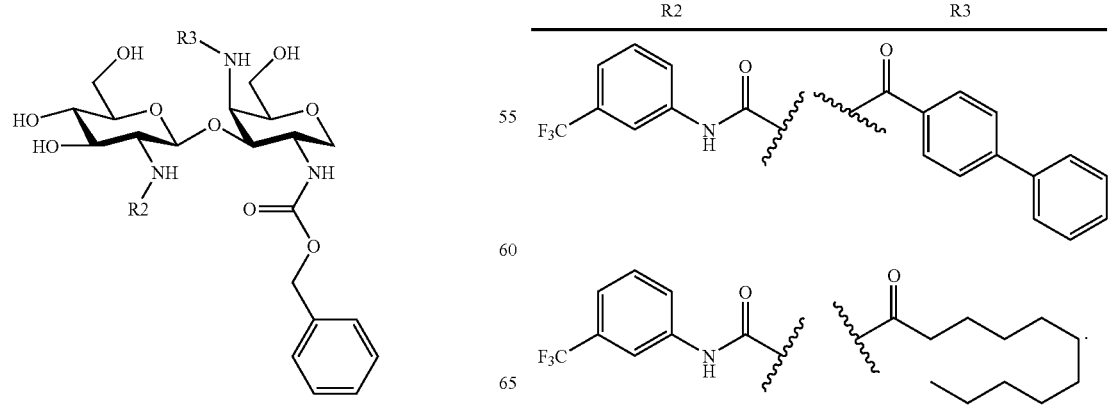

wherein:

| R2 | R3 |
|---|---|
| 3-(trifluoromethyl)phenylaminocarbonyl | 4-biphenylcarbonyl |
| 3-(trifluoromethyl)phenylaminocarbonyl | decanoyl |

11. The method of claim 1, wherein the bacteria is *Staphylococcus aureus* and the compound is

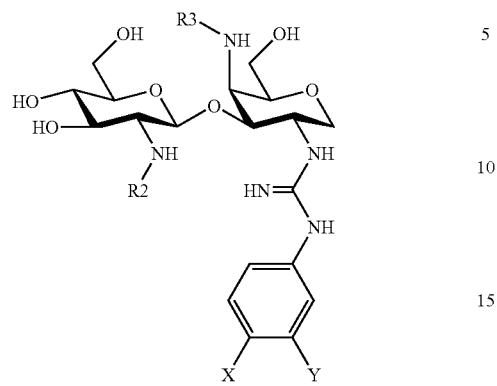

wherein:

| X | Y | R2 | R3 |
|---|---|---|---|
| H | CF₃ | 4-fluorophenyl amidine | 4-biphenylcarbonyl |
| H | CF₃ | 4-methylphenylsulfonyl | undecanoyl |
| H | CF₃ | 4-methylphenylsulfonyl | 4-biphenylcarbonyl |
| H | CF₃ | 4-methylphenylsulfonyl | H |
| H | CF₃ | 3-(trifluoromethyl)phenyl amide | undecanoyl |
| H | CF₃ | 3-(trifluoromethyl)phenyl amidine | undecanoyl |

-continued
| X | Y | R2 | R3 |
|---|---|---|---|
| H | CF₃ | 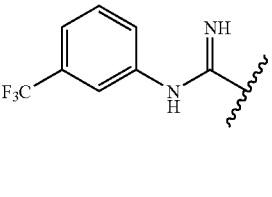 | 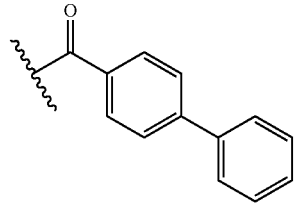 |
| H | CF₃ | 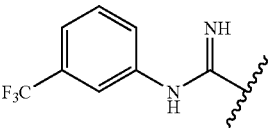 | 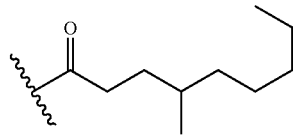 |
| H | CF₃ | 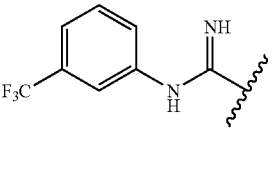 | 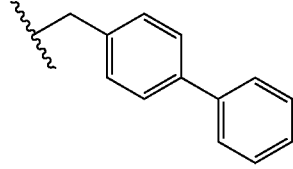 |
| H | CF₃ | 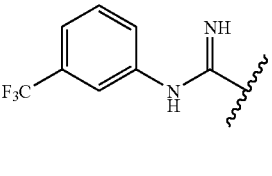 | 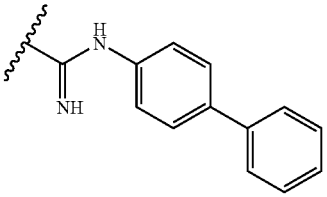 |
| H | CF₃ | 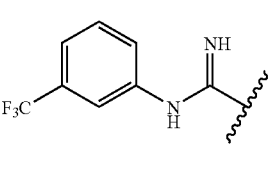 | 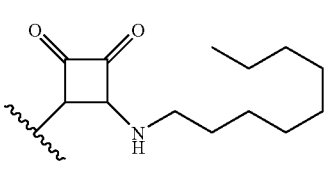 |
| H | CF₃ | 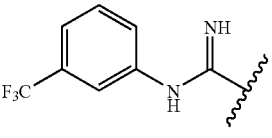 | 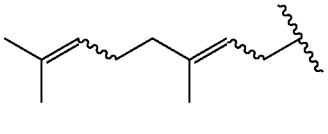 |
| H | CF₃ | 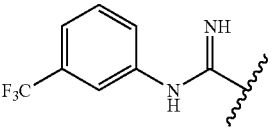 | 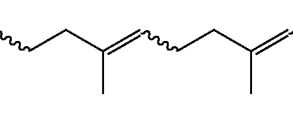 |
| H | CF₃ | 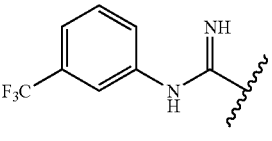 | 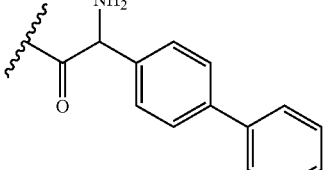 |

| X | Y | R2 | R3 |
|---|---|---|---|
| H | CF₃ | 3-CF₃-phenyl-C(=NH)NH- | -C(=O)CH(NH₂)CH₂-(4-biphenyl) |
| F | H | 3-CF₃-benzoyl | -C(=O)(CH₂)₁₀CH₃ |
| F | H | benzyl-O-C(=O)- | -C(=O)(CH₂)₁₀CH₃ |
| F | H | 4-F-phenyl-NH-C(=NH)- | -C(=O)(CH₂)₁₀CH₃ |
| F | H | 4-methylphenyl-SO₂- | -C(=O)(CH₂)₁₀CH₃ |
| F | H | 4-F-phenyl-NH-C(=O)- | -C(=O)(CH₂)₁₀CH₃ |
12. The method of claim 1, wherein the bacteria is *Staphylococcus aureus* and the compound is
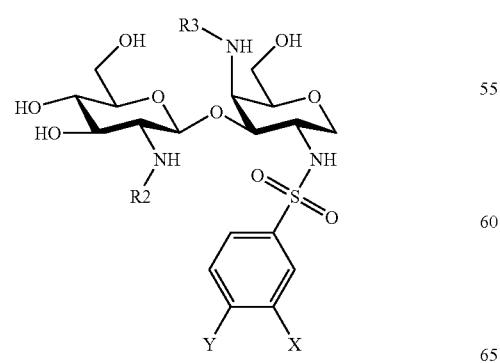

wherein:

| X | Y | R2 | R3 |
|---|---|----|----|
| CF$_3$ | H | 3-(trifluoromethyl)phenylsulfonyl | 4-phenylbenzoyl |
| CF$_3$ | H | 3-(trifluoromethyl)phenylamido | 4-phenylbenzoyl |
| H | CH$_3$ | 3-(trifluoromethyl)phenylketo | decanoyl |
| H | CH$_3$ | 3-(trifluoromethyl)phenylamido | 4-phenylbenzoyl |
| H | CH$_3$ | 3-(trifluoromethyl)phenylamido | decanoyl |

13. The method of claim 1, wherein the bacteria is *Staphylococcus aureus* and the compound is selected from the group consisting of:

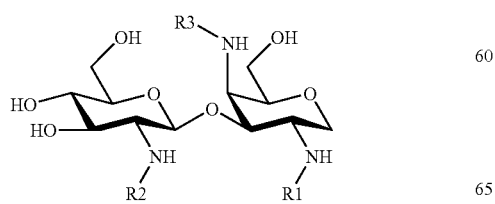

wherein
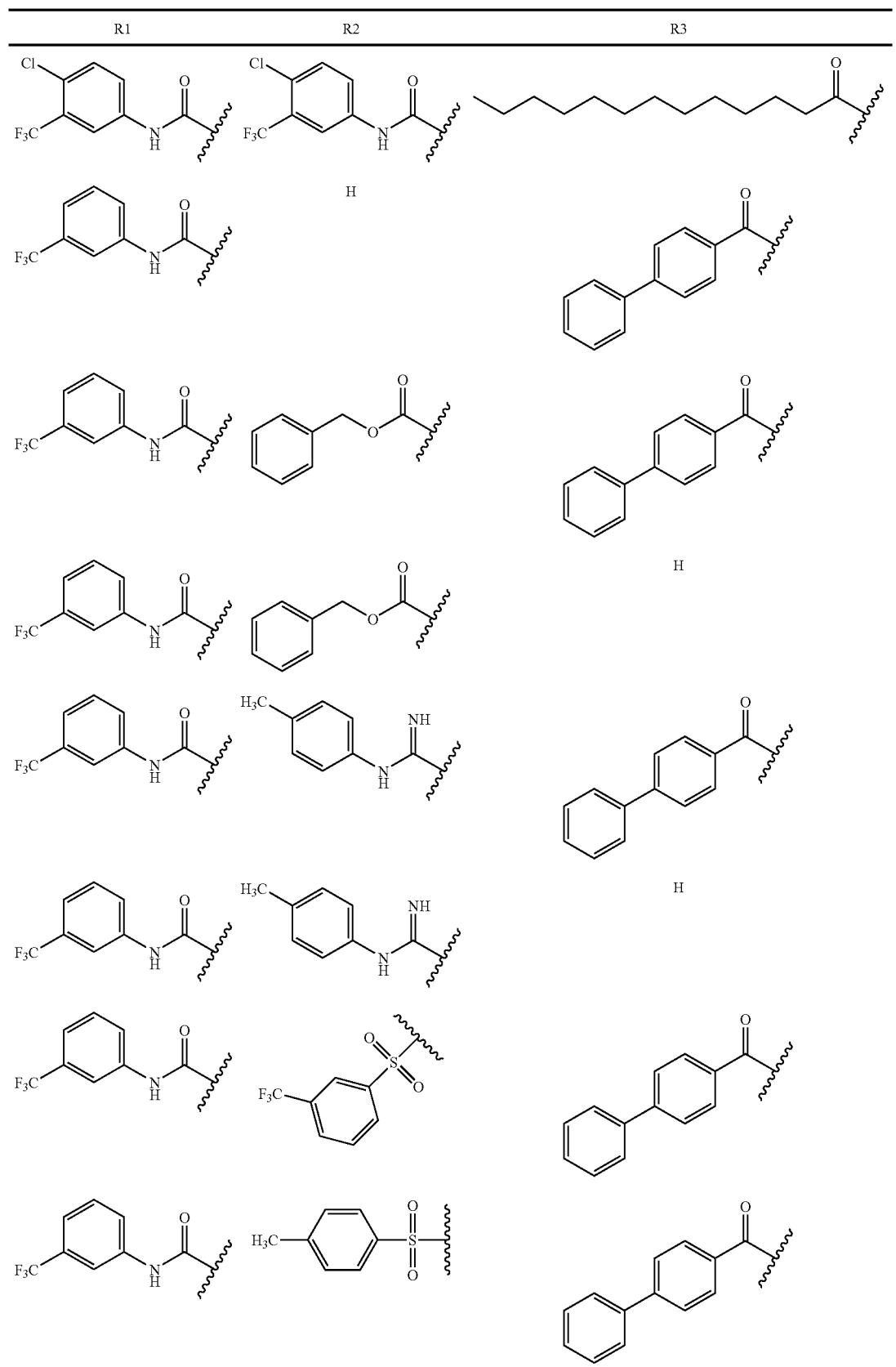

| R1 | R2 | R3 |
| --- | --- | --- |
| 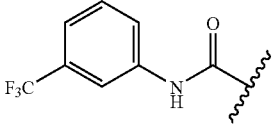 | 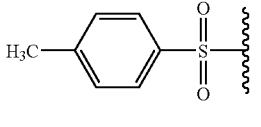 | H |
| 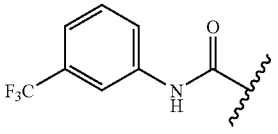 | 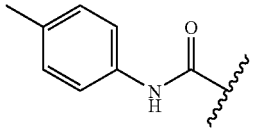 | 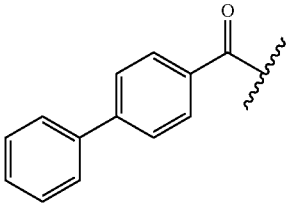 |
| 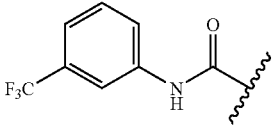 | 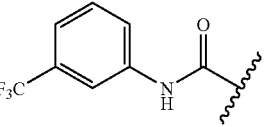 | 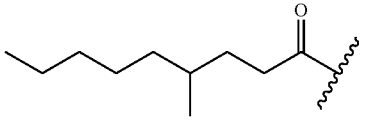<br>n-decyl |
| 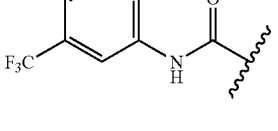 | 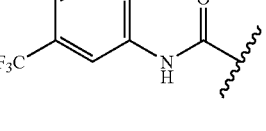 | 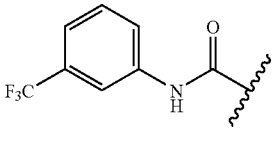 |
| 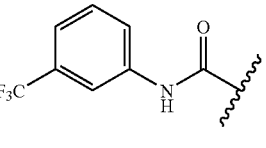 | 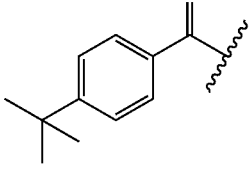 | 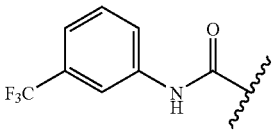 |
| 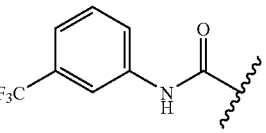 | 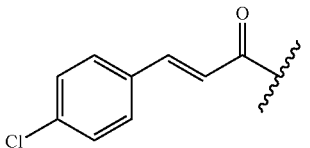 | 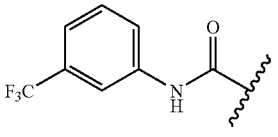 |
| 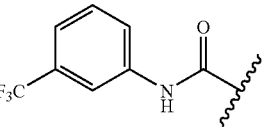 | 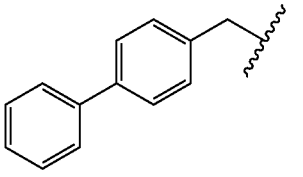 | 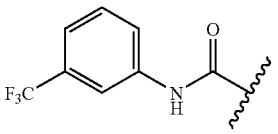 |
| 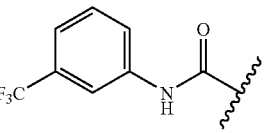 | 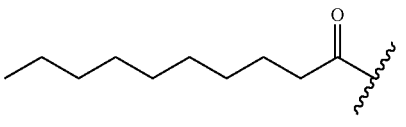 | 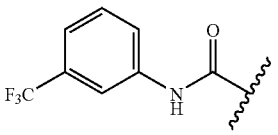 |

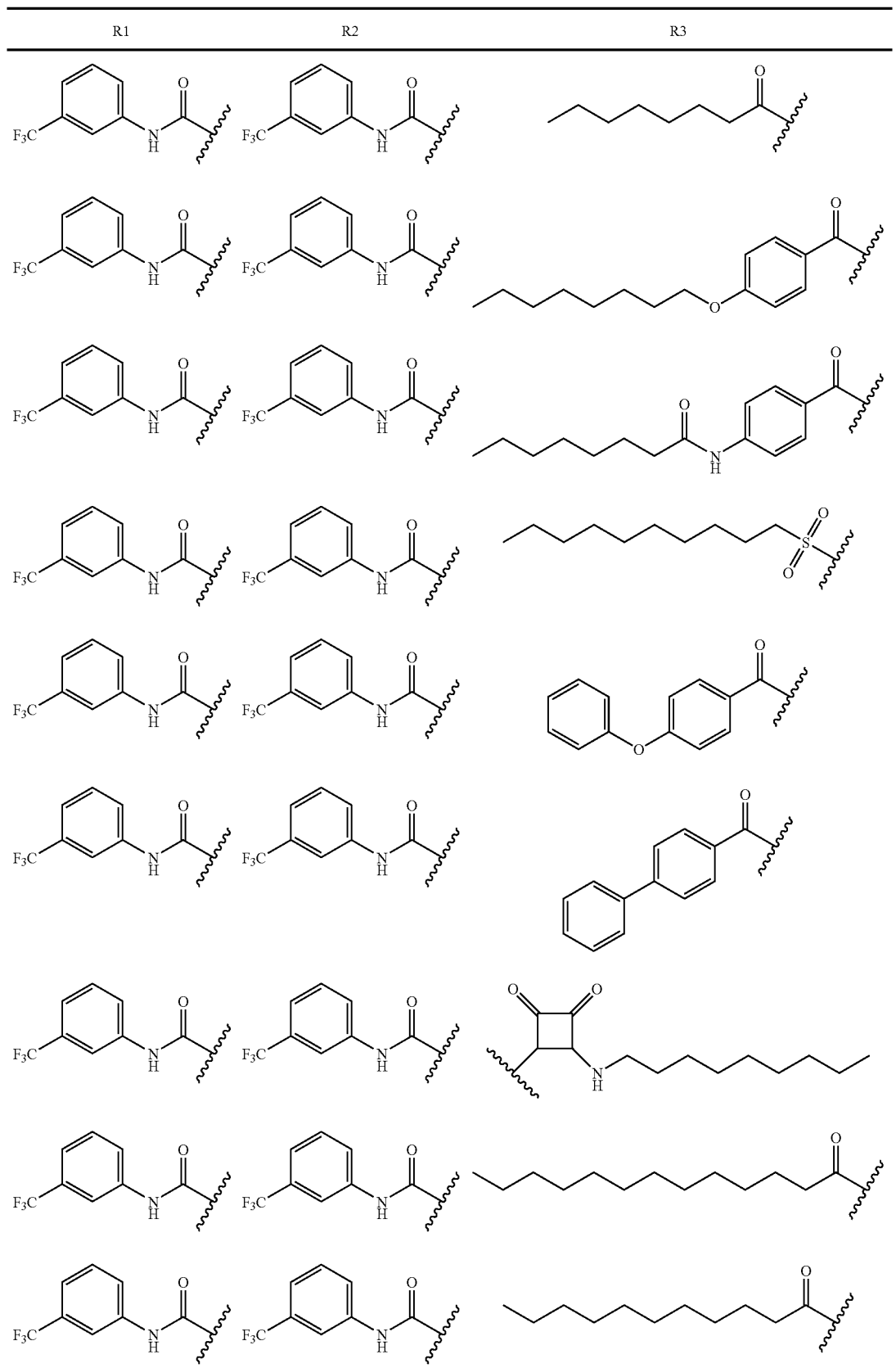

-continued
| R1 | R2 | R3 |
|---|---|---|
| 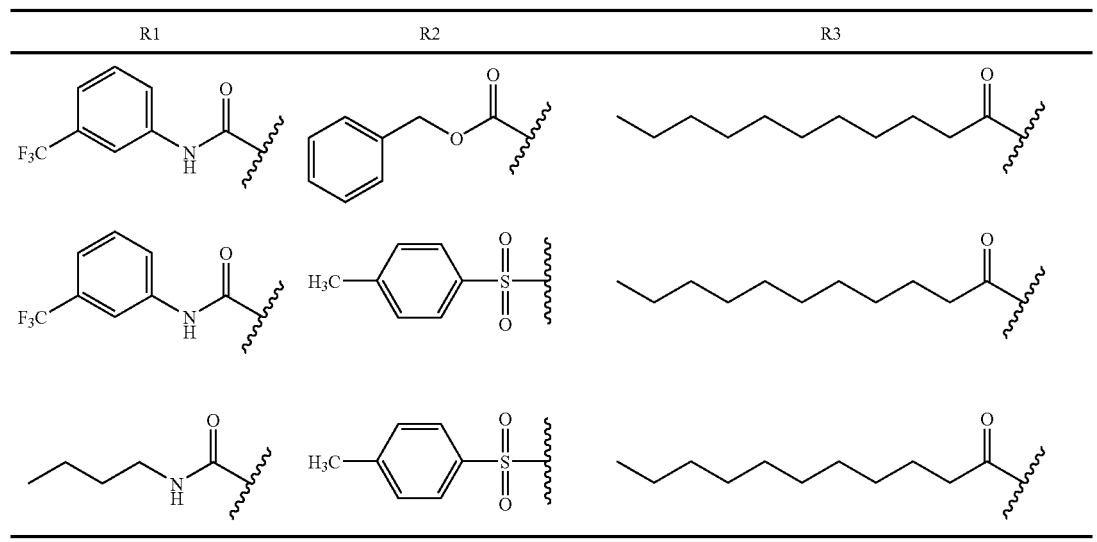 | | |
and
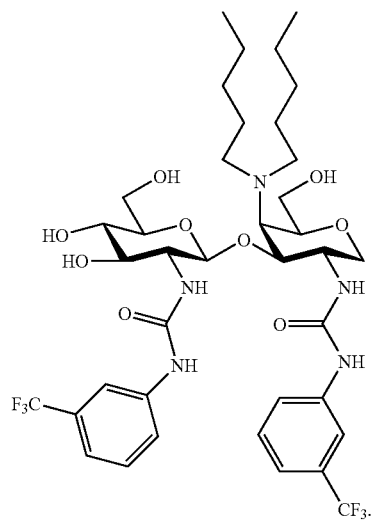
14. The method of claim 1, wherein the bacteria is *E. coli* and the compound is
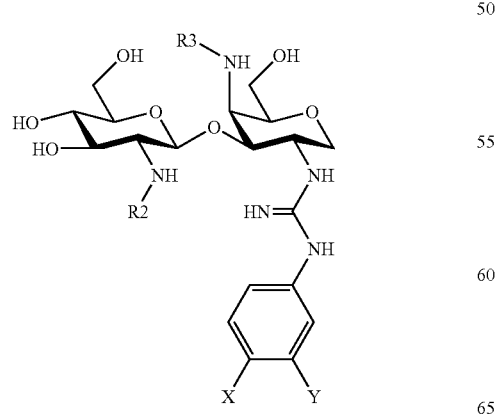

wherein:

| X | Y | R2 | R3 |
|---|---|---|---|
| H | CF$_3$ | 4-methylphenylsulfonyl | decanoyl |
| H | CF$_3$ | 4-methylphenylsulfonyl | 4-phenylbenzoyl |
| H | CF$_3$ | N-(3-trifluoromethylphenyl)amidino | decanoyl |
| H | CF$_3$ | N-(3-trifluoromethylphenyl)amidino | 4-phenylbenzoyl |
| H | CF$_3$ | N-(3-trifluoromethylphenyl)amidino | 4-methylnonanoyl |
| H | CF$_3$ | N-(3-trifluoromethylphenyl)amidino | 2-(4-phenylphenyl)ethyl |
| H | CF$_3$ | N-(3-trifluoromethylphenyl)amidino | N-(4-phenylphenyl)amidino |
| H | CF$_3$ | N-(3-trifluoromethylphenyl)amidino | 3-(octylamino)-4-oxocyclobut-1-enyl (squarate) |

-continued
| X | Y | R2 | R3 |
|---|---|---|---|
| H | CF₃ | 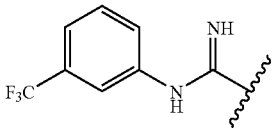 | 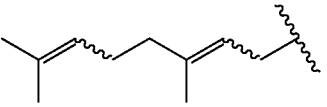 |
| H | CF₃ | 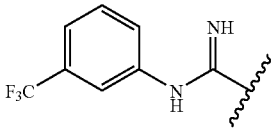 | 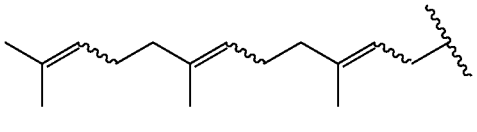 |
| H | CF₃ | 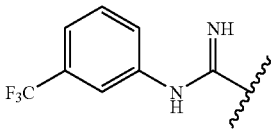 | 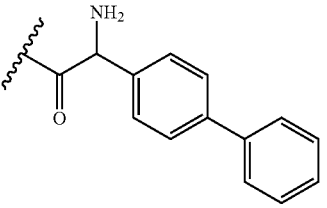 |
| H | CF₃ | 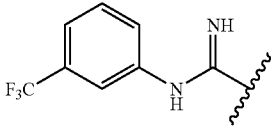 | 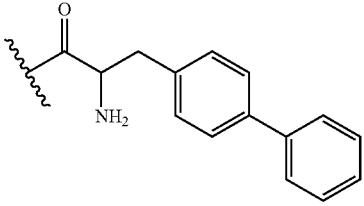 |
| H | CF₃ | 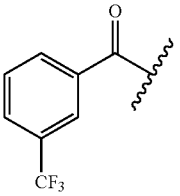 | 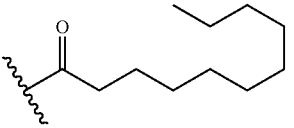 |
| H | CF₃ | 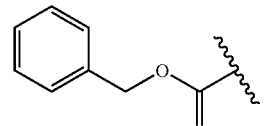 | 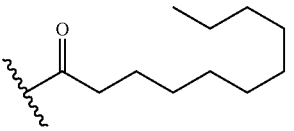 |
| H | CF₃ | 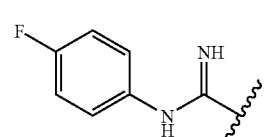 | 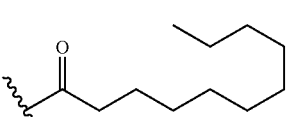 |
| H | CF₃ | 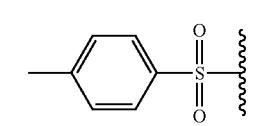 | 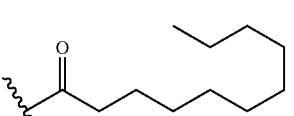 |
| H | CF₃ | 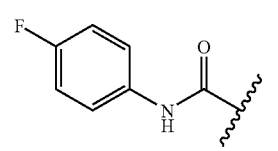 | 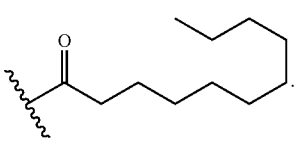 |

15. The method of claim 1, wherein the compound is

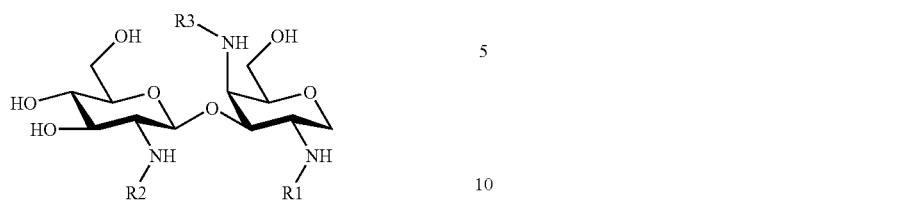

wherein:

| Compound | R1 | R2 | R3 |
|---|---|---|---|
| 42 | 4-Cl-3-CF₃-C₆H₃-NH-C(O)- | 4-Cl-3-CF₃-C₆H₃-NH-C(O)- | -C(O)-(CH₂)₁₃-CH₃ |
| 51 | 3-CF₃-C₆H₄-NH-C(O)- | 4-CH₃-C₆H₄-SO₂- | -C(O)-(CH₂)₁₃-CH₃ |
| 56 | 3-CF₃-C₆H₄-NH-C(O)- | 3-CF₃-C₆H₄-NH-C(O)- | n-decyl |
| 65 | 3-CF₃-C₆H₄-NH-C(O)- | 3-CF₃-C₆H₄-NH-C(O)- | 4-(CH₃(CH₂)₇C(O)NH)-C₆H₄-C(O)- |
| 67 | 3-CF₃-C₆H₄-NH-C(O)- | 3-CF₃-C₆H₄-NH-C(O)- | glutamic acid derivative with octanoylamide |
| 68 | 3-CF₃-C₆H₄-NH-C(O)- | 3-CF₃-C₆H₄-NH-C(O)- | -C(O)-(CH₂)₁₂-CH₃ |
| 69 | 3-CF₃-C₆H₄-NH-C(O)- | 3-CF₃-C₆H₄-NH-C(O)- | -SO₂-(CH₂)₉-CH₃ |

-continued
| Compound | R1 | R2 | R3 |
|---|---|---|---|
| 70 | 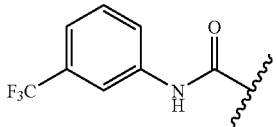 | 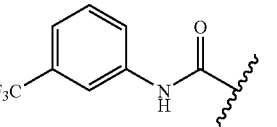 | 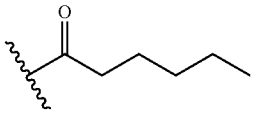 |
| 73 | 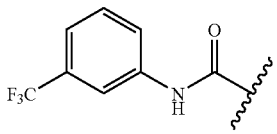 | 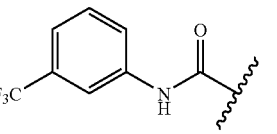 | 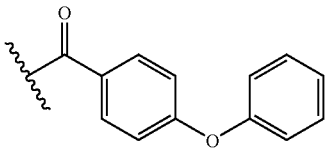 |
| 74 | 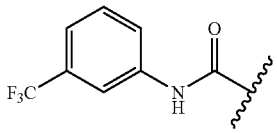 | 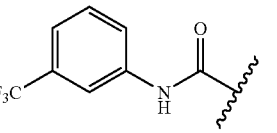 | 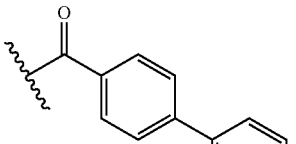 |
| 75 | 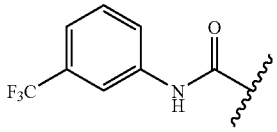 | 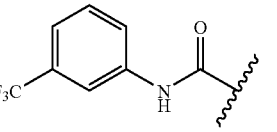 | 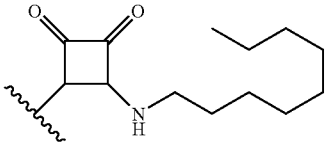 |
| 76 | 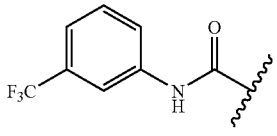 | 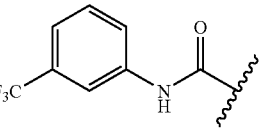 | 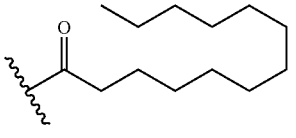 |
| 77 | 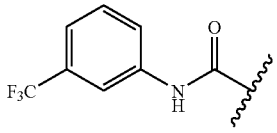 | 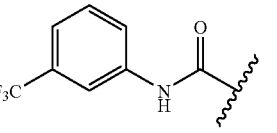 | 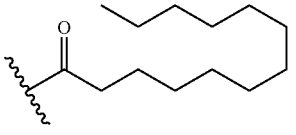 |
and the bacteria is *Micrococcus luteus*.
16. The method of claim 1, wherein the compound is
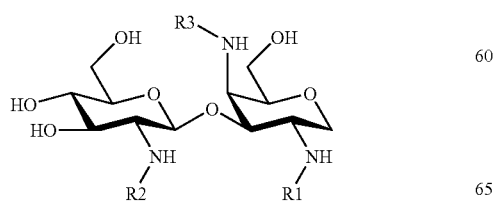

wherein:
| Compound | R1 | R2 | R3 |
|---|---|---|---|
| 42 | 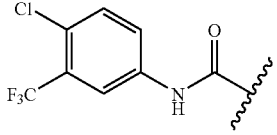 | 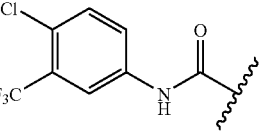 | 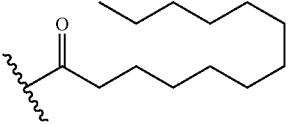 |
| 51 | 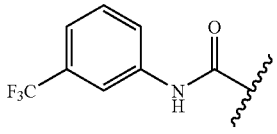 | 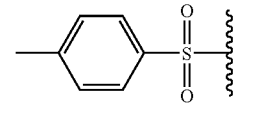 | 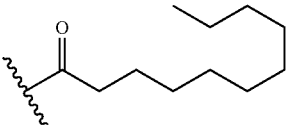 |
| 56 | 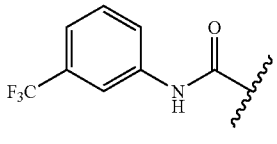 | 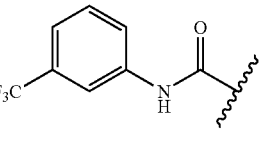 | n-decyl |
| 65 | 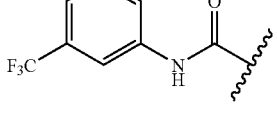 | 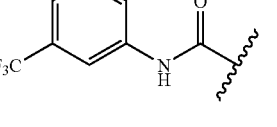 | 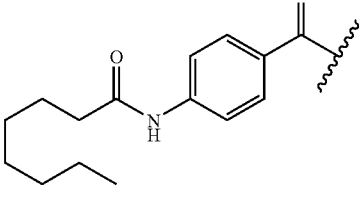 |
| 67 | 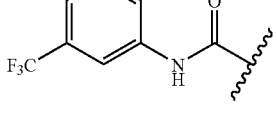 | 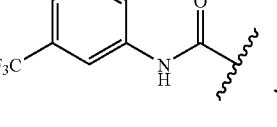 | 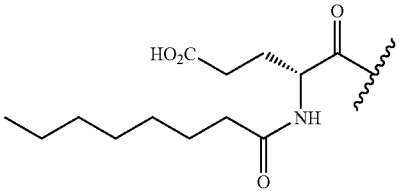 |
| 68 | 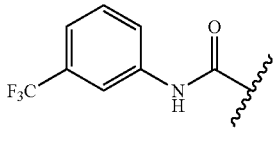 | 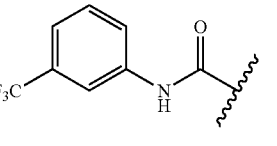 | 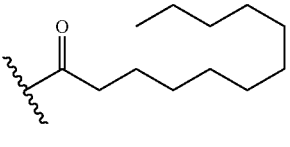 |
| 69 | 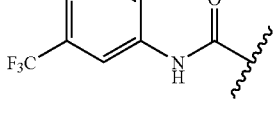 | 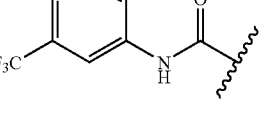 | 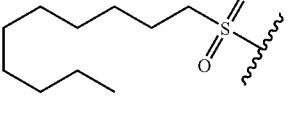 |
| 70 | 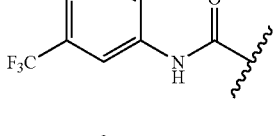 | 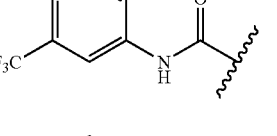 | 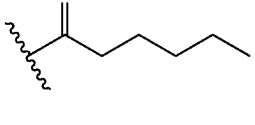 |
| 73 | 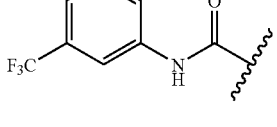 | 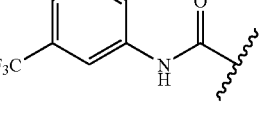 | 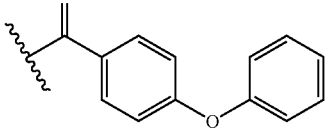 |

-continued

| Compound | R1 | R2 | R3 |
|---|---|---|---|
| 74 | 3-CF₃-C₆H₄-NH-C(O)- | 3-CF₃-C₆H₄-NH-C(O)- | 4-phenylbenzoyl |
| 75 | 3-CF₃-C₆H₄-NH-C(O)- | 3-CF₃-C₆H₄-NH-C(O)- | 2,3-dioxo-4-(octylamino)cyclobutyl |
| 76 | 3-CF₃-C₆H₄-NH-C(O)- | 3-CF₃-C₆H₄-NH-C(O)- | long-chain acyl |
| 77 | 3-CF₃-C₆H₄-NH-C(O)- | 3-CF₃-C₆H₄-NH-C(O)- | long-chain acyl | and the bacteria is *Staphylococcus aureus*.

17. The method of claim 1, wherein the compound is

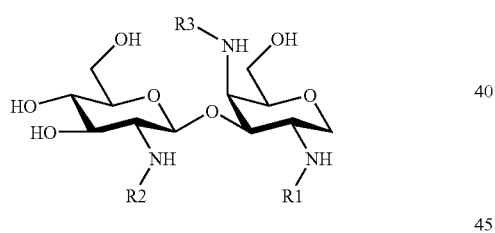

wherein:

| Compound | R1 | R2 | R3 |
|---|---|---|---|
| 42 | 4-Cl-3-CF₃-C₆H₃-NH-C(O)- | 4-Cl-3-CF₃-C₆H₃-NH-C(O)- | long-chain acyl |
| 51 | 3-CF₃-C₆H₄-NH-C(O)- | 4-methylphenylsulfonyl | long-chain acyl |

-continued

| Compound | R1 | R2 | R3 |
| --- | --- | --- | --- |
| 56 | F3C-C6H4-NH-C(O)- | F3C-C6H4-NH-C(O)- | n-decyl |
| 67 | F3C-C6H4-NH-C(O)- | F3C-C6H4-NH-C(O)- | HO2C-CH2CH2-CH(NH-C(O)-C7H15)-C(O)- |
| 68 | F3C-C6H4-NH-C(O)- | F3C-C6H4-NH-C(O)- | long-chain alkyl ketone |
| 69 | F3C-C6H4-NH-C(O)- | F3C-C6H4-NH-C(O)- | n-alkyl-SO2-CH2- |
| 73 | F3C-C6H4-NH-C(O)- | F3C-C6H4-NH-C(O)- | 4-phenoxybenzoyl |
| 74 | F3C-C6H4-NH-C(O)- | F3C-C6H4-NH-C(O)- | 4-biphenylcarbonyl |
| 75 | F3C-C6H4-NH-C(O)- | F3C-C6H4-NH-C(O)- | 3,4-dioxo-2-(decylamino)cyclobutyl |
| 76 | F3C-C6H4-NH-C(O)- | F3C-C6H4-NH-C(O)- | long-chain alkyl ketone |
| 77 | F3C-C6H4-NH-C(O)- | F3C-C6H4-NH-C(O)- | long-chain alkyl ketone | and wherein the bacteria is *Staphylococcus aureus* MRSA.

18. The method of claim 1, wherein the compound is

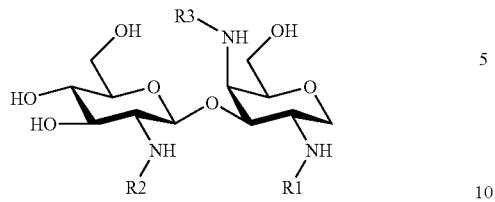

wherein:

| Compound | R1 | R2 | R3 |
|---|---|---|---|
| 42 | 4-Cl-3-CF₃-C₆H₃-NH-C(O)- | 4-Cl-3-CF₃-C₆H₃-NH-C(O)- | long chain alkyl ketone |
| 51 | 3-CF₃-C₆H₄-NH-C(O)- | 4-methylphenyl-SO₂- | long chain alkyl ketone |
| 56 | 3-CF₃-C₆H₄-NH-C(O)- | 3-CF₃-C₆H₄-NH-C(O)- | n-decyl |
| 65 | 3-CF₃-C₆H₄-NH-C(O)- | 3-CF₃-C₆H₄-NH-C(O)- | 4-(octanoylamino)phenyl ketone |
| 67 | 3-CF₃-C₆H₄-NH-C(O)- | 3-CF₃-C₆H₄-NH-C(O)- | N-octanoyl glutamyl |
| 68 | 3-CF₃-C₆H₄-NH-C(O)- | 3-CF₃-C₆H₄-NH-C(O)- | long chain alkyl ketone |
| 69 | 3-CF₃-C₆H₄-NH-C(O)- | 3-CF₃-C₆H₄-NH-C(O)- | decyl sulfonyl |

-continued
| Compound | R1 | R2 | R3 |
|---|---|---|---|
| 70 | F3C-C6H4-NHC(O)- | F3C-C6H4-NHC(O)- | hexyl ketone |
| 73 | F3C-C6H4-NHC(O)- | F3C-C6H4-NHC(O)- | 4-phenoxybenzoyl |
| 74 | F3C-C6H4-NHC(O)- | F3C-C6H4-NHC(O)- | 4-biphenylcarbonyl |
| 75 | F3C-C6H4-NHC(O)- | F3C-C6H4-NHC(O)- | squaramide-octyl |
| 76 | F3C-C6H4-NHC(O)- | F3C-C6H4-NHC(O)- | long-chain acyl |
| 77 | F3C-C6H4-NHC(O)- | F3C-C6H4-NHC(O)- | long-chain acyl |
and the bacteria is *Enterococcus faecalis*.
19. The method of claim 1, wherein the compound is
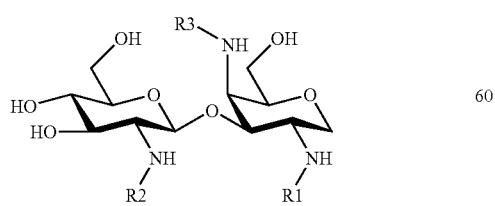

wherein

| Compound | R1 | R2 | R3 |
|---|---|---|---|
| 42 | 4-Cl-3-(CF₃)-C₆H₃-NH-C(O)- | 4-Cl-3-(CF₃)-C₆H₃-NH-C(O)- | -C(O)-(CH₂)₁₁-CH₃ (tridecanoyl) |
| 51 | 3-(CF₃)-C₆H₄-NH-C(O)- | 4-methylphenyl-SO₂- | -C(O)-(CH₂)₉-CH₃ (undecanoyl) |
| 56 | 3-(CF₃)-C₆H₄-NH-C(O)- | 3-(CF₃)-C₆H₄-NH-C(O)- | n-decyl |
| 65 | 3-(CF₃)-C₆H₄-NH-C(O)- | 3-(CF₃)-C₆H₄-NH-C(O)- | 4-(octanoylamino)phenyl-C(O)- |
| 67 | 3-(CF₃)-C₆H₄-NH-C(O)- | 3-(CF₃)-C₆H₄-NH-C(O)- | (S)-N-octanoyl-glutamyl (HO₂C-CH₂-CH₂-CH(NH-C(O)-(CH₂)₆-CH₃)-C(O)-) |
| 68 | 3-(CF₃)-C₆H₄-NH-C(O)- | 3-(CF₃)-C₆H₄-NH-C(O)- | -C(O)-(CH₂)₁₁-CH₃ |
| 69 | 3-(CF₃)-C₆H₄-NH-C(O)- | 3-(CF₃)-C₆H₄-NH-C(O)- | n-decyl-SO₂- |
| 70 | 3-(CF₃)-C₆H₄-NH-C(O)- | 3-(CF₃)-C₆H₄-NH-C(O)- | -C(O)-(CH₂)₄-CH₃ (hexanoyl) |
| 73 | 3-(CF₃)-C₆H₄-NH-C(O)- | 3-(CF₃)-C₆H₄-NH-C(O)- | 4-phenoxybenzoyl |

-continued
| Compound | R1 | R2 | R3 |
|---|---|---|---|
| 74 | 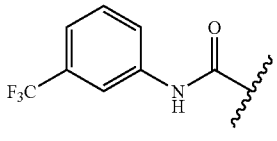 | 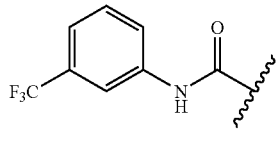 | 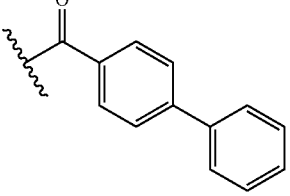 |
| 75 | 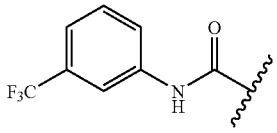 | 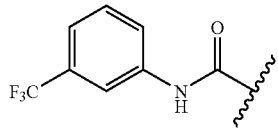 | 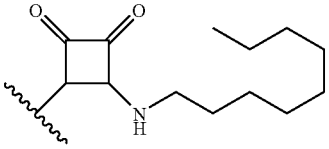 |
| 76 | 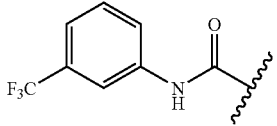 | 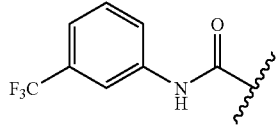 | 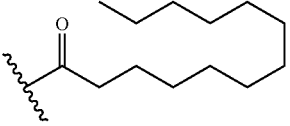 |
| 77 | 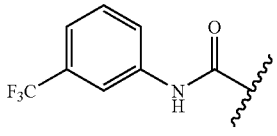 | 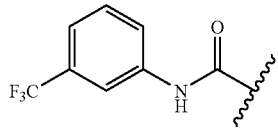 | 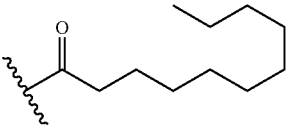 |
and wherein the bacteria is *Enterococcus faecalis* Vancomycin resistant.
20. The method of claim 1, wherein the compound is
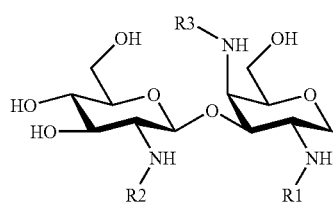
wherein:
| Compound | R1 | R2 | R3 |
|---|---|---|---|
| 42 | 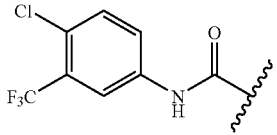 | 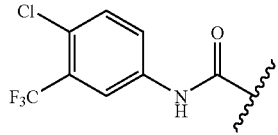 | 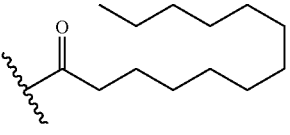 |
| 51 | 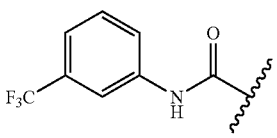 | 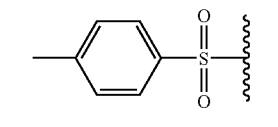 | 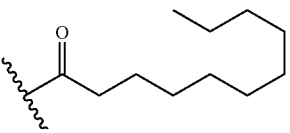 |

-continued

| Compound | R1 | R2 | R3 |
|---|---|---|---|
| 56 | 3-(trifluoromethyl)phenyl-NH-C(O)- | 3-(trifluoromethyl)phenyl-NH-C(O)- | n-decyl |
| 65 | 3-(trifluoromethyl)phenyl-NH-C(O)- | 3-(trifluoromethyl)phenyl-NH-C(O)- | 4-(octanoylamino)benzoyl |
| 67 | 3-(trifluoromethyl)phenyl-NH-C(O)- | 3-(trifluoromethyl)phenyl-NH-C(O)- | N-octanoyl-glutamyl |
| 68 | 3-(trifluoromethyl)phenyl-NH-C(O)- | 3-(trifluoromethyl)phenyl-NH-C(O)- | tridecanoyl |
| 69 | 3-(trifluoromethyl)phenyl-NH-C(O)- | 3-(trifluoromethyl)phenyl-NH-C(O)- | n-decylsulfonyl |
| 70 | 3-(trifluoromethyl)phenyl-NH-C(O)- | 3-(trifluoromethyl)phenyl-NH-C(O)- | hexanoyl |
| 73 | 3-(trifluoromethyl)phenyl-NH-C(O)- | 3-(trifluoromethyl)phenyl-NH-C(O)- | 4-phenoxybenzoyl |
| 74 | 3-(trifluoromethyl)phenyl-NH-C(O)- | 3-(trifluoromethyl)phenyl-NH-C(O)- | biphenyl-4-carbonyl |
| 75 | 3-(trifluoromethyl)phenyl-NH-C(O)- | 3-(trifluoromethyl)phenyl-NH-C(O)- | 2-(decylamino)-3,4-dioxocyclobut-1-yl |

-continued

| Compound | R1 | R2 | R3 |
|---|---|---|---|
| 76 | 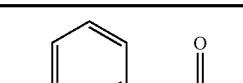 | 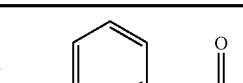 | 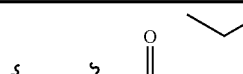 |
| 77 | 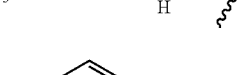 | 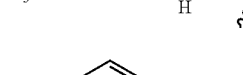 |  | and the bacteria is *Streptococcus pyogenes*.

21. A method of inhibiting a bacterial infection in a mammal comprising administering to said mammal an effective amount of a compound of General Formula (I), General Formula (I)

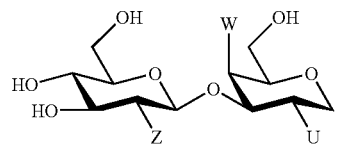

wherein

U and Z are independently selected from the group consisting of: —OR, —NHR, and —NR(R),

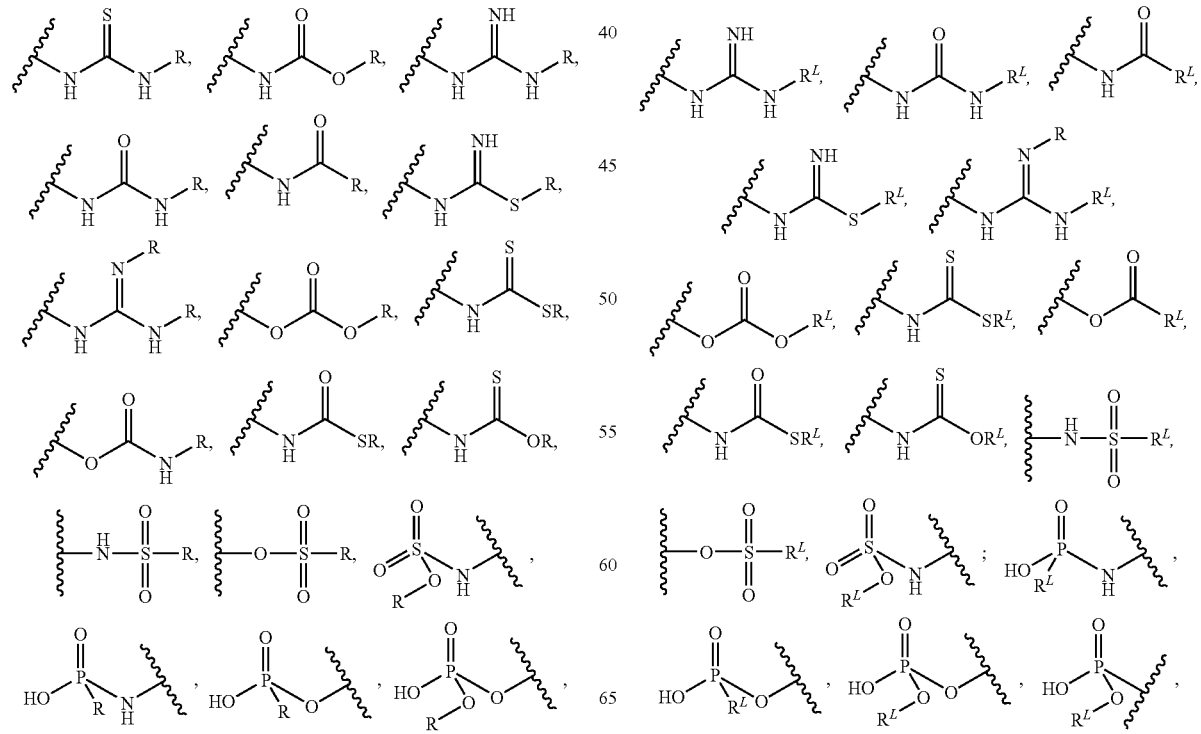

-continued

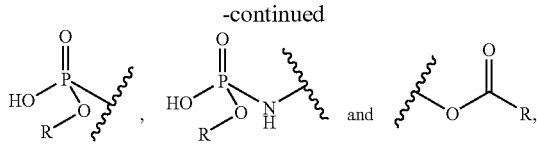

wherein R may be the same or different, R is a moiety of not more than 20 carbon atoms independently selected from the group consisting of alkyl, alkenyl, alkynyl, heteroalkyl, aryl, heteroaryl, arylalkyl and heteroarylalkyl;

W is independently selected from the group consisting of —$OR^L$, —$NHR^L$, —$NR^LR$, -continued
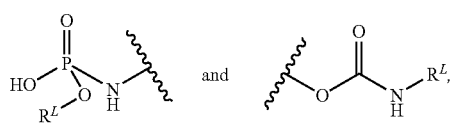
wherein $R^L$ is a substituted or unsubstituted, linear or branched moiety of between 3 and 55 carbon atoms selected from the group consisting of: alkyl, heteroalkyl, arylalkyl, and alkylaryl chain.
22. The method of claim 1, wherein the bacterium is a resistant or susceptible strain of a *Micrococcus, Streptococcus, Enterococcus* or *Staphylococcus*.
* * * * *